(12) United States Patent
Collins

(10) Patent No.: US 8,821,377 B2
(45) Date of Patent: Sep. 2, 2014

(54) LAPAROSCOPIC SURGERY

(76) Inventor: Justin Collins, Chertsey (GB)

( * ) Notice: Subject to any disclaimer, the term of this patent is extended or adjusted under 35 U.S.C. 154(b) by 39 days.

(21) Appl. No.: 13/606,874

(22) Filed: Sep. 7, 2012

(65) Prior Publication Data

US 2013/0253267 A1  Sep. 26, 2013

Related U.S. Application Data

(60) Provisional application No. 61/531,968, filed on Sep. 7, 2011.

(51) Int. Cl.
*A61B 1/00* (2006.01)
*A61F 5/44* (2006.01)
*A61B 17/00* (2006.01)
*A61B 19/10* (2006.01)

(52) U.S. Cl.
USPC ........... 600/104; 600/115; 600/121; 128/898; 604/328; 606/114

(58) Field of Classification Search
CPC ................. A61B 1/018; A61B 1/3132; A61B 2017/00557; A61B 2017/00287; A61B 2017/320775; A61B 2017/3486
USPC .......... 600/104, 114–116, 121; 128/850, 898; 604/264, 327, 328; 606/1, 114
See application file for complete search history.

(56) References Cited

U.S. PATENT DOCUMENTS

| | | | |
|---|---|---|---|
| 5,037,379 A | 8/1991 | Clayman et al. | |
| 5,368,545 A * | 11/1994 | Schaller et al. | 128/850 |
| 5,611,803 A | 3/1997 | Heaven et al. | |
| 5,618,296 A | 4/1997 | Sorensen et al. | |
| 6,270,505 B1 | 8/2001 | Yoshida et al. | |
| 6,350,267 B1 | 2/2002 | Stefanchik | |
| 2007/0135780 A1 | 6/2007 | Pagedas | |
| 2009/0299137 A1 * | 12/2009 | Gal et al. | 600/116 |

\* cited by examiner

*Primary Examiner* — Anhtuan T Nguyen
*Assistant Examiner* — Aaron B Fairchild
(74) *Attorney, Agent, or Firm* — Fanelli Haag & Kilger PLLC

(57) ABSTRACT

The present invention relates to a method of laparoscopic surgery, and a kit which could be used in laparoscopic and robotic surgery.

15 Claims, 2 Drawing Sheets

LAPAROSCOPIC SURGERY

This application claims the benefit of the filing date of U.S. Appl. No. 61/531,968, filed Sep. 7, 2011, the entirety of which is fully incorporated by reference herein.

FIELD OF THE INVENTION

The present invention relates to a method of laparoscopic surgery, and a kit which could be used in laparoscopic and robotic surgery.

BACKGROUND OF THE INVENTION

Laparoscopic surgery, also known as minimal access, minimally invasive or keyhole surgery, is a modern surgical technique. During laparoscopic surgery operations are performed through small incisions, usually 0.5 to 1.5 cm in length. This is in contrast to traditional open surgery where a much longer incision would be made to perform the same operation.

Minimal access surgery also known as minimally invasive surgery (MIS) which includes laparoscopic and robotic surgery and which utilises minimal sized incisions is becoming increasingly popular, with more and more routine operations such as nephrectomy and cystectomy being carried out with this type of surgery.

Laparoscopic and robotic surgery have many advantageous over traditional surgery, which are mainly due to the minimally invasive nature and small incision length. These advantages include reduced pain, reduced blood loss, reduced scarring, fewer post-operative infections and shorter recovery times.

However, one of the limitations of MIS concerns the removal of a relatively large specimen. This is particularly common in oncological procedures such as laparoscopic radical nephrectomy, colectomy, cystectomy and hysterectomy. In most oncological and many other laparoscopic procedures, the specimen to be removed from the patient's body is too large to be able to remove it easily through the normal incision made for a laparoscopic port (called a port incision). In this situation the surgeon currently has two options.

The first option is to make a further, larger, incision or to enlarge the port incision so that the specimen can be removed as a whole. Usually this requires an incision of 10 cm long or longer, and sometimes the incision can be longer than 20 cm. Hence, this reduces the advantages of using laparoscopic surgery, which are listed above, and in some cases means that there is actually minimal benefit in performing laparoscopic surgery, over traditional open surgery.

The second option is to morcellate the specimen inside the body cavity into pieces that are small enough to be removed through the port incision. A major concern with this approach is that it is not always possible to ensure that every trace of the morcellated specimen is removed. Where the specimen is benign, leaving a part of the specimen in the body cavity may lead to infection as the tissue breaks down and acts as a source for infection. There is even more risk involved in this method when the specimen is malignant, since any escape of malignant cells can lead to tumour seeding. Tumour seeding can occur at the site from which the specimen is removed. In addition, since the surgical plume travels throughout the surgical site, metastasis can occur at any point where 'raw' areas are located, such as any of the port sites. In view of these risks, most large specimens are still extracted in one piece through a separate incision.

There have, however, been some attempts to reduce the risks associated with morcellating the specimen inside the body cavity, by placing a bag around the specimen before it is morcellated. Such a device is generally known as an Endo-Bag. Endo-Bags normally comprise a plastic bag, with an opening at one end. They are inserted through the port incision, the specimen is then passed into the bag and can be pulled through the incision in the bag, optionally after being cut up. Some Endo-Bags, such as that shown in U.S. Pat. No. 6,270,505 comprise a plastic tube with an opening at both ends. A drawstring is provided at one end, which is closed once the specimen is inside the tube. The most common type of morcellation is via a blunt instrument which crushes the tissue and it is then pulled out in pieces through the port incision.

While the use of Endo-Bags can reduce the risks, Endo-Bags do not enclose the whole surgical plume, particularly when they are closed only by means of a drawstring at one end. Therefore, the risk of tumour seeding and port site metastasis remains. In addition, Endo-Bags are normally made from one or two layers of a thin flexible film of a polymer such as polyethylene or polyurethane. These can be ruptured by a sharp instrument, including those needed to morcellate the specimen. This possibility also presents the danger of tumour seeding.

The present invention is concerned with addressing these problems and with providing an improved solution for the removal of large specimens during laparoscopic surgery. In particular, the present invention aims to provide a method of laparoscopic surgery which allows for morcellation of a specimen inside the body cavity, with a reduced risk of tumour seeding.

SUMMARY OF THE INVENTION

A first aspect of the invention provides a method of carrying out laparoscopic surgery to remove a specimen from the body of a patient, the method comprising the steps of:

(i) providing a laparoscopic port which comprises tubular housing, an inflatable cuff around the distal end of the housing, an insufflation nozzle which is in fluid communication with the inflatable cuff, and a locking ring which can be passed over the proximal end of the housing and secured relative to the housing at different points along the length of the housing, and positioning the laparoscopic port through the skin of the patient so that the distal end of the laparoscopic port is in a body cavity and the proximal end of the laparoscopic port is outside the patient;

(ii) providing a laparoscopic bag which has a top portion and a body portion, and only one opening which is in the top portion, and passing the laparoscopic bag through the laparoscopic port into the body cavity;

(iii) placing the specimen into the body portion of laparoscopic bag;

(iv) passing the top portion of the laparoscopic bag out through the skin of the patient, before or after removing the tubular housing of the laparoscopic port from the patient's body;

(v) inserting the tubular housing of the laparoscopic port back inside the top portion of the laparoscopic bag so that the distal end of the housing is in the body cavity;

(vi) inflating the inflatable cuff of the tubular housing using the insufflation nozzle, passing the locking ring over the proximal end of the housing, and locking the locking ring against the housing so that the top portion of the laparoscopic bag and the skin of the patient are gripped between the inflatable cuff and the locking ring;

(vii) attaching the top portion of the laparoscopic bag to a sheath, which comprises a tube of medical-grade waterproof material;
(viii) placing a mechanical morcellator through the sheath into the laparoscopic bag;
(ix) morcellating the specimen under irrigation in the laparoscopic bag; and
(x) removing the morcellated specimen from the body of the patient through the top of the laparoscopic bag and the sheath.

A second aspect of the invention provides a kit which comprises a sheath, and a laparoscopic bag.

The method of the present invention addresses the problems associated with the removal of large specimens from the body during laparoscopic surgery by mechanically morcellating the specimen under irrigation in a confined space. Although irrigation is known from various different medical procedures, in previous methods of mechanically morcellating a specimen in a laparoscopic bag, irrigation has not usually been used. Irrigation is advantageous as the pressure of the liquid maintains the bag in a fully open position, provided that the irrigation occurs within a confined space. This confined space is provided in the present invention by gripping the bag between the inflatable cuff and the locking ring of the port. This provides a controlled and constant space for the surgeon to operate in, which is highly favourable. Further, it means that the morcellator is less likely to accidentally come into contact with and cut the sides of the bag. The constant circulation of liquid provided by irrigation causes the specimen to "bobble" and rotate away from the bag, allowing safe morcellation. In addition, irrigating with a clear liquid improves the visibility for the surgeon, as debris will be irrigated away.

In the method of the invention, the top portion of the laparoscopic bag is held between the skin and the port, away from the morcellator. The structure provided by the port in holding the top portion of the bag against the skin, helps to ensure that the laparoscopic bag does not come into contact with the morcellator. Irrigation in this environment is also improved, because of the structure provided by having the port inside the top section of the bag. Since the top section of the bag is trapped between the port and the skin, irrigation liquids can not escape from the top of the bag, without going through the port. This allows for constant and controlled irrigation, which is highly desirable in any kind of surgery.

In the method of the invention, the top portion of the laparoscopic bag is attached to a sheath. The morcellated material is taken away from the body through the sheath. This means that, even if some of the irrigation liquids are not sucked up by the morcellator, and spill out of the top of the bag, they do not come into contact with the skin of the patient, and are instead sealed inside the sheath, from where they can be safely removed. This provides an important safety feature, and means that morcellation can be carried out safely using this method.

The fact that the method of the present invention allows for the safe morcellation of a large specimen in the body cavity means that laparoscopic surgery can be carried out using this method without either having to make a large incision to remove a specimen, or risk tumour seeding. This represents a significant advance in medical technology and will bring widespread patient benefits, meaning that patients can benefit fully from the advantages of minimally invasive laparoscopic surgery, without risking tumour seeding or port-site metastasis.

In more detail, the method of the present invention comprises the following steps.

(i) Providing a laparoscopic port and positioning the laparoscopic port through the skin of the patient so that the distal end of the laparoscopic port is in a body cavity and the proximal end of the laparoscopic port is outside the patient. Any laparoscopic port can be used that comprises tubular housing, an inflatable cuff around the distal end of the housing, an insufflation nozzle which is in fluid communication with the inflatable cuff, and a locking ring, which can be passed over the proximal end of the housing, and secured relative to the housing at different points along the length of the housing. The benefits of this type of housing are discussed below.

In addition to the tubular housing the laparoscopic port may also contain exterior housing, external to the tubular housing, and/or removable channels within the tubular housing.

The body cavity is insufflated to provide enough space to carry out the surgical procedure.

(ii) Providing a laparoscopic bag, and passing the laparoscopic bag through the laparoscopic port into the body cavity. Suitable laparoscopic bags are discussed below. When a laparoscopic port according to the present invention with removable channels is used, the channels can be removed before the bag is passed through. Where the exterior housing is present, the tubular housing can be removed, leaving the exterior housing in place which the laparoscopic bag is passed through. The tubular housing of the port is then replaced so that the body cavity space can be re-insufflated.

(iii) Placing the specimen into the body portion of the laparoscopic bag. This is done using conventional manipulation devices. A camera is preferably provided on the laparoscopic equipment, so that the surgeon can see the specimen and guide it into the bag.

(iv) Passing the top portion of the laparoscopic bag out through the skin of the patient, before or after removing the tubular housing of the laparoscopic port from the patient's body. Where the exterior housing of the port is present, the tubular housing can be removed before the top portion of the bag, leaving the exterior housing in place so that the opening and top portion of the bag are pulled through the exterior housing. If the exterior housing does not exist, the tubular housing can be removed before passing the bag out of the body, and the bag can simply be passed through the skin, or the bag can be passed out of the body though the tubular housing, which is then removed.

(v) Inserting the tubular housing of the laparoscopic port back inside the top portion of the laparoscopic bag so that the distal end of the housing is in the body cavity.

(vi) Inflating the inflatable cuff of the tubular housing using the insufflation nozzle. This allows the inflated cuff to be pulled up against the abdominal wall and secured firmly in position by passing the locking ring over the proximal end of the housing, and locking the locking ring against the housing so that the top portion of the bag and the skin of the patient are gripped between the inflatable cuff and the locking ring.

(vii) Attaching the top portion of the laparoscopic bag to a sheath, which comprises a tube of medical-grade waterproof material. In this way, the morcellated specimen is removed from the body of the patient through the top portion of the laparoscopic bag and the sheath. This is advantageous, since transportation through the sheath will enable safe transportation of the specimen and the whole surgical plume away from the patient.

(viii) Placing a mechanical morcellator through the sheath into the laparoscopic bag. By mechanical morcellator we mean a motorised morcellator such as the VersaCut Tissue Morcellator System. Such morcellators reduce the specimen to a pulp, so that it can easily be removed from the body, even through a relatively narrow port. In contrast sometimes non-mechanical morcellation is used in surgery, such a manual morcellation where a specimen is broken down into smaller fragments using graspers that are not motorised. The mechanical morcellators generally includes a suction device to carry irrigation liquid away from the bag.

(ix) Morcellating the specimen under irrigation in the laparoscopic bag. The irrigation is highly beneficial as discussed above. Any conventional method of irrigation can be used. Irrigation is generally achieved by connecting a bag of irrigation liquid so that it can flow into the laparoscopic bag, usually via a tube to the scope.

Often in medicine, irrigation liquid is positioned above the area to be irrigated, and simply uses gravity to push through the irrigation liquid. Occasionally irrigation can be used under pressure by applying a pressure device, such as a pressure cuff, that inflates to a predetermined pressure around the bag to squeeze out the irrigant under pressure. In the present invention, it is normally necessary to use pressure to irrigate the laparoscopic bag during morcellation. Irrigation can be carried out at any suitable pressure, and is usually carried out at an irrigation pressure of between 20 mmHg and 300 mmHg, preferably around 100 mmHg Any suitable clear liquid can be used for the irrigation liquid. The irrigation liquid is generally water, a saline solution, or glycine or glucose isotonic solutions. Suitable solutions are sold by the company Baxter.

In the method of the present invention, the specimen is irrigated during morcellation, by circulating a liquid around the bag. This causes the bag to gently inflate and the specimen to float and rotate in the irrigation liquid and keeps it away from the sides of the bag. This is an important safety feature, as it makes it less likely for the inner layer of the bag to be ruptured by the morcellator. Morcellating the specimen under irrigation in the laparoscopic bag also enables improved vision of the specimen as it will help clear away debris. The specimen is morcellated, generally under direct vision, until it is small enough to be removed via the port site.

(x) Removing the morcellated specimen from the body of the patient through the top portion of the laparoscopic bag and the sheath. The specimen is removed by suction on the morcellator during morcellation. The specimen is morcellated until the remains are small enough to be removed from the body whilst still contained in the bag in continuity with the sheath through the port site incision without the need to extend the incision size. In this way, as discussed below, the sheath enables the morcellated material to be carried away safely.

As noted above, the morcellation preferably takes place under direct vision of the surgeon. This improves the safety of the operation. Currently it is thought that morcellators that have built-in cameras do not exist, but they may do in the future. Therefore morcellation under direct vision requires a nephroscope or equivalent. This then allows the surgeon to judge when the inner layer of the bag has been breached and is why, in the preferred embodiment, the bag layers have an inner white layer to reflect light and enable optimum vision and why the middle layer is an 'unnatural' colour such as luminous green so that it is obvious if the inner layer is breached. If a breech has occurred, the bag can then be removed via a larger incision without compromising tumour cell spillage as the outer layer will still be intact. The nephroscope would go down the tubular housing, and specifically down one of the channels, where they are present. The irrigation would go down the second channel so as to irrigate the space. It is advantageous to have the irrigation and morcellator pass through separate channels as when thy irrigation enters the bag from a different angle from the nephroscope, this improves rotation of the specimen inside the bag. The second channel could also potentially be used for other instruments.

An example of a nephroscope that could be used with the present invention is as follows. The nephroscope has a 5 mm working channel and the diameter of the nephroscope is 26 Fr (8.66 mm diameter). The nephroscope lens is attached to a camera as standard operating kit so the image can be seen on a screen. The nephroscope also has irrigation but using the second channel for irrigation is advantageous as it allows you to change the irrigation direction. If irrigation is in parallel with the suction then the specimen is less likely to spin or rotate, so this will help to view the specimen from different angles, potentially to preserve certain elements of the specimen for histology that are of interest and also to keep the specimen away from the bag. The second channel also has the potential for secondary use for alternative instruments for example to use a grasper to hold the tissue in position.

Laparoscopic ports are known in the art, as they are used in all laparoscopic and robotic operations. Accordingly, the basic housing of a port is well known to a person skilled in the art.

In a preferred embodiment, the tubular housing has two ports with an oval cross section. Instrumentation such as a morcellator, irrigation scope and camera can be passed through the channels. It is preferred that the channels are removable from the housing, so that they can be removed leaving the oval shaped frame of the housing, to allow bigger objects, such as a rolled-up laparoscopic bag, to pass through the port.

The tubular housing of the port of the present invention is preferably oval, and can be anything from 5 mm to 40 mm along the longest diameter, but is preferably around 20 mm along the longest diameter. Alternatively, a standard circular or oval port with a 10 mm or 15 mm diameter can be used.

The tubular housing has an inflatable cuff around the distal end of the housing and an insufflation nozzle which is in fluid communication with the inflatable cuff. By distal end of the housing we mean the end portion, usually the end third, that would be furthest into the patient during an operation. By the proximal end we mean the end portion, usually the end third, that would be furthest away from the patient during an operation. When inflated, the inflatable cuff resembles a ring around the outside of the distal end of the housing, that can abut the tissue between the abdominal cavity and the skin through which the housing is inserted.

In this embodiment of the invention the laparoscopic port also comprises a locking ring, which can be passed over the proximal end of the housing, and secured relative to the housing at different points along the length of the housing, by any suitable securing means, for example with a ring which overlaps and then locks in place with a clasp similar to a watch bracelet clasp. The locking ring is positioned relative to the inflatable cuff so that they grip the skin, thereby securing the housing in place. The advantage of having an adjustable locking ring is that it can be secured to provide a tight seal in patients with varying depths of subcutaneous fat or abdominal muscle so that the bag is secured and the irrigation liquid can be enclosed within the bag. This is important for controlling the amount and pressure of the irrigation fluid within the bag and also reducing the risks of tumour seeding or infection.

As noted above, the method comprises the step of attaching the top portion of the laparoscopic bag to one end of a sheath. The sheath that can be used comprises a tube of medical-grade waterproof material. By medical grade, we mean suitable for use in medical applications, such as laparoscopic surgery. The waterproof material can be the same as the waterproof material used for the laparoscopic bag or can be different. The sheath material should be such that it acts as an effective barrier keeping the surgical plume within the bag and sheath. The surgical plume consists of small particles, tumour cells, liquids, aerosols and any other materials including biological materials that may move out of the bag during the laparoscopic procedure and specimen removal.

The sheath can be as long as desired, and from a safety perspective should be long enough to pass over the cabling for the equipment (morcellator, nephroscope and irrigation tube etc) to well away from the patient.

The sheath has at one end attaching means for attaching it to the laparoscopic bag. Any suitable attaching means can be used that maintain a waterproof connection between the sheath and the laparoscopic bag. In one preferred embodiment, the attaching means is either a ridge that is capable forming a zip-lock fit with housing on a laparoscopic bag, or housing that is capable of forming a zip-lock fit with a ridge on a laparoscopic bag i.e. a freezer-bag style attachment. In another preferred embodiment, the attaching means could be adhesive such that the sheath opening and the bag opening both have an adhesive strip which is made accessible after pulling off protective tape. The sheath and the bag are sealed by pressing the adhesive strips together. In another preferred embodiment, the attaching means could be through locking rings such as in an embroidery hoop where both the sheath and the bag are secured between two rings of only slightly different circumference which are then tightened and locked in place by a screw or other locking mechanism.

When a sheath is used, the laparoscopic bag also has attaching means on the top portion which cooperate with the attaching means on the sheath. As above, in a preferred embodiment the laparoscopic bag has attaching means that comprises either a ridge that is capable of forming a zip-lock fit with housing on a sheath, or housing that is capable of forming a zip-lock fit with a ridge on a sheath.

The method of the present invention uses a laparoscopic bag which comprises a top portion and a body portion, which are defined in that there is an opening in the top portion, but not in the bottom portion. Having only one opening, which is in the top portion, means that when the top portion is passed out of the body cavity through a port, the body portion of the laparoscopic bag that remains in the body will be entirely enclosed. The laparoscopic bag therefore provides an environment which, under irrigation, can remain constant. This represents a significant advantage over methods that use traditional Endo-Bags that comprise a tube with a drawstring closure at one end.

It is preferred that the bag comprises a rectangular shape when flat, and a tubular shape when open, with one end sealed. The body portion is the section of the bag adjacent the sealed end, with the top portion being the section of the bag at the end which comprises the opening. Having a rectangular shaped bag is advantageous since, during use, the bag can be rolled up and passed through a laparoscopic port. A rectangular shaped bag is able to be rolled up neatly and efficiently in terms of space, compared to a bag of another shape.

The top portion will, during use, become neck-shaped as a result of the top of the bag being pulled back through the port after the bag is opened. Where the cross-sectional area of the body portion and top portion is the same, which is preferred, the bag can be a tubular shape. When in use, the top portion is approximately tubular, and the body portion shape is caused by the specimen and the pressure differences caused by the morcellation process.

As noted above, the top portion of the laparoscopic bag comprises an opening. This is the only opening in the bag, there are no other openings.

In one embodiment of the invention a three-layered bag with an inner layer that is waterproof, a middle layer which is resistant to morcellation, and an outer layer which is waterproof can be used. Each of the three layers encompasses substantially the whole bag, and not merely a strip or section thereof. The use of such laparoscopic bags is advantageous since it provides in a convenient manner an enclosed environment for safe morcellation of large specimens from which traces of specimen cannot escape. In previous Endo-Bags with one or two waterproof layers there is a risk that the layers will be ruptured by a sharp instrument, such as that needed to morcellate the specimen. However, with the laparoscopic bag of the present invention, the middle layer is resistant to morcellation, so will not be ruptured during normal use. Therefore, even if the inner layer is ruptured, the outer layer will be protected from rupture by the middle layer and will still provide an enclosed environment from which traces of the specimen cannot escape.

In this embodiment the inner and outer layers are waterproof, and can be made of any suitable material. The inner and outer layers are usually made from a thin flexible film of a polymer such as polyethylene or polyurethane. The inner and outer layers can be made of the same or different material from one another. Such films are well known to the person skilled in the art. The inner layer may be white in colour to reflect light and aid visibility when the bag is in use in the body cavity.

The middle layer may be brightly coloured, for example an unnatural luminous colour which could be orange or green, so that if the white inner layer is breached the colour of the middle layer shows through and it is evident that the inner layer has been breached. The middle layer is resistant to morcellation. By this we mean that the middle layer is made of a material that can not be easily penetrated by the mechanical morcellation process.

Any material that is resistant to morcellation can be used as the middle layer. Suitable materials for use as the middle layer that are resistant to morcellation include a woven mesh of synthetic material such as polyurethane, a film or mesh of heavy-duty plastic, a mesh of metallic wires or a mesh of carbon fibres. In a preferred embodiment, the middle layer comprises a mesh.

In this embodiment, if the inner layer is ruptured, the middle layer will protect the outer layer from also being ruptured, so the specimen will still be enclosed as noted above. It would, however, be advantageous for the surgeon to know that the inner layer has been ruptured, so that they can document the incident, check the outer layer, and ensure that there has been no escape of the specimen. Accordingly, in a preferred embodiment of the invention the inner layer is white and the middle layer is coloured, textured, or patterned or the middle layer is transparent and the outer layer is coloured, textured, or patterned. This means that if in inner layer is ruptured, the middle layer or the outer layer will be visible to a camera which is usually used during laparoscopic surgery, to enable the surgeon to take appropriate action. Preferably the middle layer is brightly coloured, most preferably luminous green or the middle layer is transparent and the outer layer is brightly coloured, preferably luminous green.

In a different embodiment, the laparoscopic bag is not a laparoscopic bag that comprises an inner layer which is waterproof, a middle layer which is resistant to morcellation, and an outer layer which is waterproof. Instead the bag can comprise one, two, or four or more layers, for example five or six layers. In this embodiment it is preferred that a layer that is resistant to morcellation as defined above is included. Preferably a waterproof layer as defined above it also included, exterior to the morcellation resistant layer, so that it is not possible for the morcellator to cut through all the layers allowing any of the specimen to escape. As defined above, it is preferable for the layers to have different colourings so that it is easy to detect if there has been a breech. In particular, the inner layer would be white to reflect light and give the best vision. The morcellation resistant layer, or the layer exterior to it should be brightly coloured, so as to alert the surgeon immediately to any breech of the middle layer.

The present invention also relates to a kit comprising a sheath and a laparoscopic bag. The kits also preferably includes a laparoscopic port and irrigation tubing. All components are as described above. The kit is preferably provided as a single use disposable kit. The laparoscopic bag is preferably in a collapsed state in the kit ready for use and is most preferably rolled up.

The present invention also relates to the use of a laparoscopic port, a sheath, a laparoscopic bag and an irrigation tubing in laparoscopic surgery to remove a specimen from the body of a patient. The laparoscopic port, a sheath, a laparoscopic bag and irrigation tubing are as described above.

BRIEF DESCRIPTION OF THE DRAWINGS

Embodiments of the invention will now be described with reference to the accompanying drawings, in which.

DETAILED DESCRIPTION OF EMBODIMENT(S)

Figure 1:
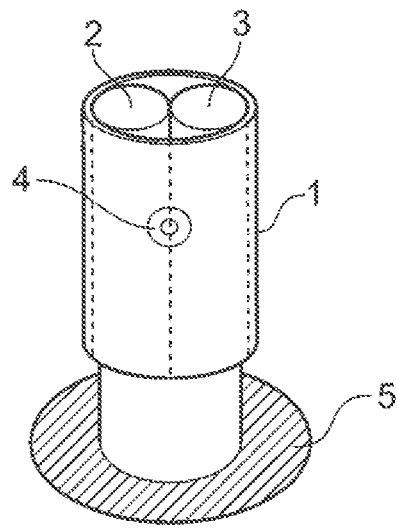
FIG. 1 shows a perspective view of a laparoscopic port according to a preferred embodiment of the present invention.
Figure 2:
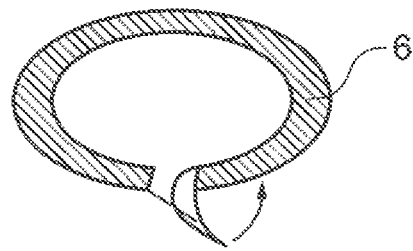
FIG. 2 shows a perspective view of a locking ring according to a preferred embodiment of the present invention.
Figure 3:
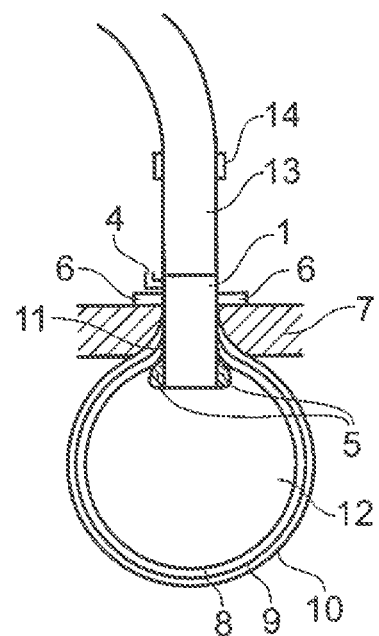
FIG. 3 shows a cross sectional view of a laparoscopic bag and a laparoscopic port according to a preferred embodiment of the present invention.

FIG. 1 shows the tubular housing 1 of a laparoscopic port, through which there are two channels, 2 and 3. The housing 1 is oval in cross section, with a largest diameter of around 20 cm. The housing has an insufflation nozzle, 4, at its proximal end which is in fluid communication with the inflatable cuff, 5. The locking ring 6, shown in FIG. 2, can be passed over the proximal end of the housing 1 and secured next to the skin 7, as shown in FIG. 3. The function of the port is to make a watertight seal around the incision, to hold the bag in place and allow to access for the morcellator, tools for morcellation such as the nephroscope and irrigation tubes.

Figure 4:
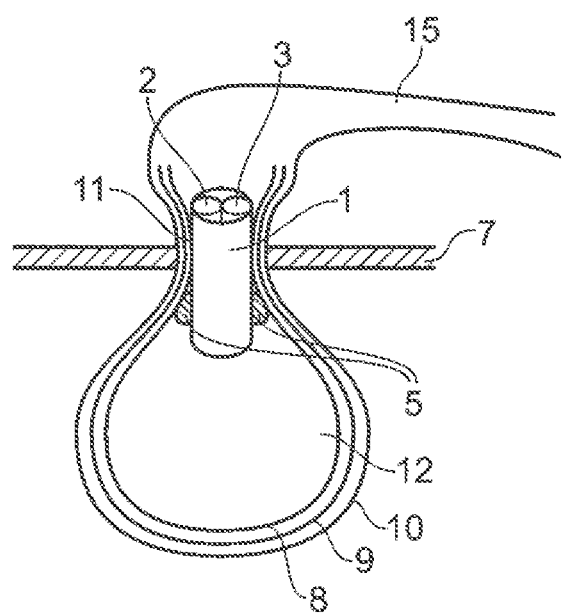
FIG. 4 shows a schematic view of a laparoscopic bag, a sheath and a laparoscopic port according to a preferred embodiment of the present invention.
Figure 5:
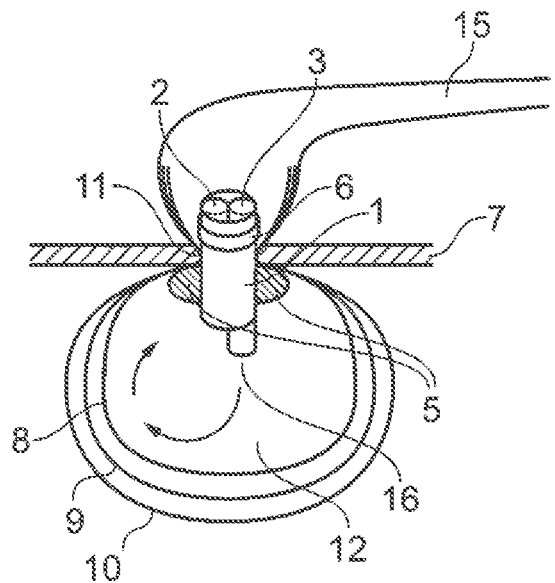
FIG. 5 view of a laparoscopic bag, a sheath and a laparoscopic port according to a preferred embodiment of the present invention.

FIGS. 3, 4 and 5, show the laparoscopic bag of a preferred embodiment of the present invention with inner layer 8, middle layer 9, and outer layer 10. A bag having 2, or 4 or more layers can also be used in the method of the invention.

In FIGS. 3, 4 and 5, the laparoscopic port housing 1 is through the skin 7 of a patient and inside the top portion 11 of the laparoscopic bag. The laparoscopic bag body portion 12 is substantially spherical. The inflatable cuff 5 is inflated. In FIGS. 3 and 5, the locking ring 6 is in place against the skin, so that the inflatable cuff 5 and the locking ring 6 grip the skin 7 and hold the port housing 1 in place.

In FIG. 3 the port housing 1 is attached to a retrieval tube 13 which allows for endoscope, irrigator and morcellator access to the specimen (not shown). This can be used in addition to the sheath, which is not present in FIG. 3. The retrieval tube has a waterproof quick attach/release joint 14 which is used after the edges of the bag are out of the incision site and the port is put in place.

In FIGS. 4 and 5 the outer layer 10 of the laparoscopic bag is attached to the sheath 15. During use, the laparoscopic bag 11 12 would be passed through the port housing 1 in collapsed form, usually rolled up, and opened inside the body cavity. The specimen, not shown, would be inserted through the top portion 11 and into the body portion 12. The port would then be removed, and reinserted inside the top portion 11 of the laparoscopic bag. The inflatable cuff 5 would be inflated, and the locking ring 6 secured over the housing, so as to grip the skin 7. A morcellator not shown would be passed through one of the channels 2 3 of the housing 1 and an irrigator 16 would be passed down the other channel. Irrigation would ensure that the specimen floats and is rotated and kept away from the inner wall 8 of the laparoscopic bag, as shown by the arrows in FIG. 5, while the specimen is morcellated.

Although the invention has been described above with reference to one or more preferred embodiments, it will be appreciated that various changes or modifications may be made without departing from the scope of the invention as defined in the appended claims.

The invention claimed is:

1. A method of carrying out laparoscopic surgery to remove a specimen from the body of a patient, the method comprising the steps of:
   (i) providing a laparoscopic port which comprises tubular housing, an inflatable cuff around the distal end of the housing, an insufflation nozzle which is in fluid communication with the inflatable cuff, and a locking ring which can be passed over the proximal end of the housing and secured relative to the housing at different points along the length of the housing, and positioning the laparoscopic port through the skin of the patient so that the distal end of the laparoscopic port is in a body cavity and the proximal end of the laparoscopic port is outside the patient;
   (ii) providing a laparoscopic bag which has a top portion and a body portion, and only one opening which is in the top portion, and passing the laparoscopic bag through the laparoscopic port into the body cavity;
   (iii) placing the specimen into the body portion of laparoscopic bag;
   (iv) passing the top portion of the laparoscopic bag out through the skin of the patient, before or after removing the tubular housing of the laparoscopic port from the patient's body;
   (v) inserting the tubular housing of the laparoscopic port back inside the top portion of the laparoscopic bag so that the distal end of the housing is in the body cavity;
   (vi) inflating the inflatable cuff of the tubular housing using the insufflation nozzle, passing the locking ring over the proximal end of the housing, and locking the locking ring against the housing so that the top portion of the bag and the skin of the patient are gripped between the inflatable cuff and the locking ring;
   (vii) attaching the top portion of the laparoscopic bag to a sheath, which comprises a tube of medical-grade waterproof material;

(viii) placing a mechanical morcellator through the sheath into the laparoscopic bag;

(ix) morcellating the specimen under irrigation in the laparoscopic bag; and (x) removing the morcellated specimen from the body of the patient through the top of the laparoscopic bag and the sheath.

2. The method according to claim 1, wherein a nephroscope is passed through the tubular housing into the bag, preferably wherein the morcellator is passed though the nephroscope.

3. The method according to claim 1, wherein the irrigation is carried out at an irrigation pressure of between 20 mmHg and 300 mmHg, preferably around 100 mmHg.

4. The method according to claim 1, wherein the irrigation liquid is water, saline solution, or a glycine or glucose isotonic solution.

5. The method according to claim 1, wherein the laparoscopic housing comprises an exterior housing, external to the tubular housing.

6. The method of claim 1, wherein the laparoscopic bag is attached to the sheath with attaching means comprises either a ridge that is capable of forming a zip-lock fit with housing on a sheath, or housing that is capable of forming a zip-lock fit with a ridge on the sheath.

7. The method of claim 1, wherein the laparoscopic port comprises two channels, and the mechanical morcellator is passed through one channel with means for direct vision of the specimen, and the irrigation tube is passed through the other channel, wherein preferably the means for direct vision of the specimen is a nephroscope.

8. The method of claim 1, wherein the mechanical morcellator includes a suction device that carries irrigation liquid away from the laparoscopic bag.

9. The method of claim 1, wherein the laparoscopic bag comprises an inner layer which is waterproof, a middle layer which is resistant to morcellation, and an outer layer which is waterproof.

10. The method of claim 9, wherein the middle layer of the laparoscopic bag comprises a film or mesh, preferably wherein the middle layer comprises a mesh, and most preferably wherein the film or mesh is made of heavy-duty plastic, metallic wires or carbon fibres.

11. The method of claim 9, wherein the inner layer of the laparoscopic bag is white and the middle layer is coloured, textured, or patterned, preferably wherein the middle layer is brightly coloured, most preferably wherein the middle layer is luminous green.

12. The method of claim 1, wherein the top portion of the laparoscopic bag is tubular, and the body portion is substantially spherical.

13. The method according to claim 1, wherein the laparoscopic bag is not a laparoscopic bag that comprises: an inner layer which is waterproof; a middle layer which is resistant to morcellation; and an outer layer which is waterproof.

14. The method according to claim 1, wherein the laparoscopic bag comprises 1, 2, 4 or 5 layers.

15. The method according to claim 14, wherein at least one of the layers is waterproof, and at least one of the layers is resistant to morcellation.

* * * * *